United States Patent [19]

Bertholet et al.

[11] Patent Number: 4,925,932
[45] Date of Patent: May 15, 1990

[54] PREPARATION OF DOUBLE SULFATE SALT OF DESOXYFRUCTOSYL SEROTONIN AND CREATININE

[75] Inventors: Raymond Bertholet, Blonay; Pierre Hirsbrunner, Les Monts-de-Corsier, both of Switzerland

[73] Assignee: Nestec S.A., Vevey, Switzerland

[21] Appl. No.: 120,394

[22] Filed: Nov. 13, 1987

Related U.S. Application Data

[62] Division of Ser. No. 756,052, Jul. 17, 1985, Pat. No. 4,722,923.

[30] Foreign Application Priority Data

Aug. 9, 1984 [CH] Switzerland ............... 3823/84

[51] Int. Cl.$^5$ ............... C08B 37/00; C07H 5/04
[52] U.S. Cl. ............... 536/55.3; 536/55
[58] Field of Search ............... 536/55, 55.3

[56] References Cited

FOREIGN PATENT DOCUMENTS 2317937 11/1978 France .
1551141 8/1979 United Kingdom .
WO/8404310 11/1984 World Int. Prop. O. .

OTHER PUBLICATIONS

J. E. Hodge et al., "Amadori Rearrangement Products", Methods in Carbohydrate Chemistry, vol. II, 1963 pp. 99–107.

P. Jayaraman, et al, "Inhibition of the Incorporation of [$^3$H] DOPA in Mycobacterium Leptae by Desoxyfructo–Serotonian", Biochemical Pharmacology vol. 29, 1980, pp. 2526–2528.

*Primary Examiner*—Ronald W. Griffin
*Assistant Examiner*—Pamela S. Webber
*Attorney, Agent, or Firm*—Vogt & O'Donnell

[57] ABSTRACT

A double sulfate salt of 1-desoxy-(5-hydroxytryptamino)-D-fructose (DFS) and 1-methylhydantoin-2-imide (creatinine) is prepared by adding creatinine to an aqueous solution of DFS containing sulfuric acid having a pH of approximately 3. The double salt may be isolated by crystallizing it in the presence of a water-miscible solvent such as ethanol. DFS may be prepared by glycosylation of 5-hydroxytryptamine with D-glucose and then adding an excess of calcium hydroxide to the glycosylation reaction medium for precipitating DFS.CA(OH)$_2$ from which the DFS may be isolated for preparing the double salt as described above. Recycling and treatment of mother liquors enables yields to be increased.

21 Claims, No Drawings

PREPARATION OF DOUBLE SULFATE SALT OF DESOXYFRUCTOSYL SEROTONIN AND CREATININE

CROSS REFERENCE TO RELATED APPLICATIONS

This is a divisional application of application Ser. No. 06/756,052, filed July 17, 1985, now U.S. Pat. No. 4,722,923.

This invention relates to a double sulfate salt of desoxyfructosyl serotonin and creatinine, to a process for the production thereof and to a medicament containing this compound.

French Patent No. 2 317 937 relates to new derivatives of serotonin (5-hydroxytryptamine), more especially the oxalate of 1-desoxy-(5-hydroxytryptamino)-D-fructose or desoxyfructosyl serotonin, hereinafter referred to as "DFS", obtained by Amadori rearrangement. In this French Patent, DFS is described as a medicament effective against platelet agglutination and in affording protection against radiation. More recently, DFS has proved to be extremely active in the treatment of leprosy (Jayaraman P.; Mahadevan P. R., Mester L., Mester M., Biochemical Pharmacology, Vol. 29, 2526-28, 1980).

It is known that, if the active substance in question is to be used as a medicament, it must be presented in a crystalline and stable unit form. However, DFS is unstable: it is in the form of a white, amorphous and non-crystallizable product which turns brown after about 1 day at ambient temperature, forming polymers. The oxalate of DFS is also amorphous, yellow in color, contains impurities and turns brown in storage which rules out its use as a medicament. Because of its high solubility in water, the oxalate has proved impossible to obtain in solid form by standard crystallization techniques using solvents, for example alcohol, the application of low temperatures, the addition of seed crystals, etc.

The present invention relates to a double sulfate salt of 1-desoxy-5-hydroxytryptamino)-D-fructose and 1-methylhydantoin-2-imide (creatinine) in crystalline form which does not have any of the disadvantages of the described compounds.

This salt is soluble in aqueous media at low temperatures and highly soluble therein at high temperatures. Since a 1% by weight aqueous solution has a pH value of 3.5, the secondary amine and imine functions, respectively, of DFS and 1-methylhydantoin-2-imide are protonated, enabling the following formula to be attributed to the salt:

A study using a polarizing optical microscope has shown that this new solid phase, which is in the form of a white crystalline powder, is composed of highly birefringent, low symmetry crystals of the monoclinic or triclinic type.

Chemical analysis has enabled the composition of the crystals to be established, leading, by application of the law of single proportions, to a double sulfate.

With a molecular weight of 585.6 and a melting range of 136°-140° C. (with decomposition), DFSCS has an apparent density of approximately 30 g/100 ml and a rotatory power $[\alpha]20/D$ of $-20.0$ to $-21.0°$ ($c=1$, water).

It is insoluble in alcohols containing 2 and more carbon atoms, ethers, esters, ketones and halogenated solvents, slightly soluble in methanol and soluble in dimethyl sulfoxide.

It is characterized by remarkable stability in the solid phase. After storage for 6 months at 45° C. in the form of capsules in a glass container, no change was observed.

The present invention also relates to a process for the production of DFSCS, characterized in that 1-methylhydantoin-2-imide is added to an aqueous solution of DFS containing sulfuric acid at a pH of approximately 3 and in that the DFSCS is separated from the reaction medium.

Separation is preferably carried out by concentration of the aqueous solution, addition of a water-miscible solvent, in which the DFSCS is insoluble, and crystallization of the DFSCS.

It is preferred to use a slight excess of creatinine in relation to the DFS, for example of from 1.1 to 1.2 times the molar quantity of DFS. The solution may be concentrated to approximately half its volume, for example, by evaporation under reduced pressure.

Acetone or $C_1-C_4$ alcohols, preferably ethanol, are advantageously used as the solvent.

The crystals formed are then separated, for example, by filtration, and dried, for example, in vacuo. After optional recrystallization, for example, from water/ethanol, filtration and drying as indicated above, the DFSCS is collected in the form of white crystals.

The DFS used as starting product may be obtained, for example, by condensation of D-glucose with 5-hydroxytryptamine, followed by Amadori rearrangement (conversion of the N-glycoside of an aldose into the N-glycoside of the corresponding ketose in the presence of an acidic or basic catalyst) using known methods (cf., "Methods in Carbohydrate Chemistry", Vol. 2, Academic Press N.Y., 1963, page 99).

It is preferred to use an excess of D-glucose of from

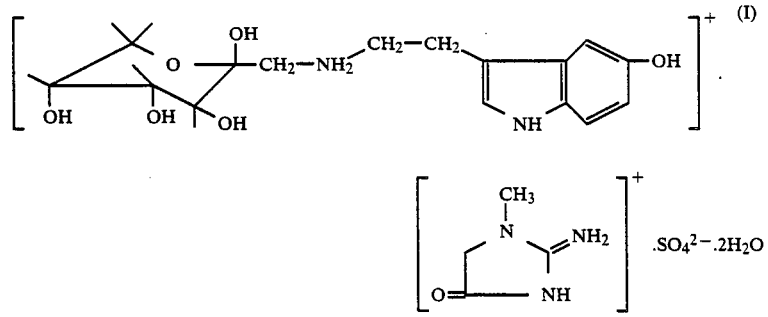

hereinafter referred to in short as "DFSCS".

1.5 to 3 times the molar quantity of serotonin present.

The serotonin is advantageously present in the form of one of its salt, for example, the hydrogenoacetate.

The reaction is carried out in an anhydrous solvent in an inert atmosphere, for example, in a nitrogen atmosphere, in order to avoid hydrolysis of the intermediate aldosylamine. The solvent should be able to solubilize the glucose and the serotonin. It is of advantage to use a lower alcohol, i.e., an alcohol containing from 1 to 4 carbon atoms, for example, methanol, ethanol or isopropanol, methanol being preferred because it provides for better selectivity of the reaction.

The reaction is preferably catalyzed by acids. The acid used as catalyst is selected from mineral or, preferably, organic acids which, depending on their type and the quantity in which they are added, enable a pH of from 3 to 5 and, preferably, a pH of 4.2 to be adjusted in the reaction medium. Acids suitable for use as catalysts include mono- or polycarboxylic acids, for example, formic acid, oxalic acid or acetic acid, formic acid being preferred.

The reaction temperature ranges from ambient temperature to the reflux temperature of the solvent.

The reaction generally lasts 30 to 150 minutes. Depending on its duration, the reaction is more or less complete and gives a mixture containing, based on the weight of the serotonin-containing species, from 60 to 83% of DFS, from 3 to 35% of residual serotonin and from 5 to 14% of secondary products. The excess glucose and the acid introduced are also found in the reaction medium.

Water is preferably added to the reaction medium and the solvent eliminated, for example, by distillation under reduced pressure. The aqueous solution is advantageously decolored, for example, with active carbon, and sulfuric acid, preferably concentrated, is added in the quantity necessary to adjust the solution to a pH of approximately 3.

Both the DFS, hydrolyzable to serotonin, and the serotonin itself may be recycled, but not the secondary products, i.e., the di- and tri-substituted derivatives and the polymers.

In one preferred variant, the reaction is interrupted after approximately 40 minutes and, after the DFSCS has been separated as described above, the serotonin is extracted from the liquid phase by ion exchange or, preferably, with a solvent. In this latter case, for example, the pH of the liquid phase is adjusted to the isoelectric point of the serotonin by addition of a strong base, for example, sodium or potassium hydroxide, i.e., to approximately 10.8, after which the serotonin is extracted with an aliphatic alcohol containing from 4 to 8 carbon atoms, for example, isobutanol or a benzyl alcohol (i.e., benzyl or methylbenzyl alcohol) and, after elimination of the solvent, the serotonin is recycled upstream of the reaction by which the DFS is formed. Advantageously, the serotonin to be recycled is converted into the form of the salt which was used for the reaction. The alcohol, for example, isobutanol, solution is thus neutralized to a pH of approximately 6, for example, with acetic acid, and the solvent is eliminated, for example, by evaporation under reduced pressure.

In one preferred embodiment of the process according to the invention for preparing the aqueous solution of DFS containing sulfuric acid, an excess of calcium hydroxide over the DFS is added to the reaction medium containing the DFS in the presence of water, an insoluble addition complex is collected and treated with an acid which precipitates calcium, the calcium is eliminated in the form of an insoluble salt, the DFS in solution is collected and sulfuric acid is added to the solution.

By adding calcium hydroxide, preferably in the form of an aqueous or aqueous-alcoholic suspension, with stirring at ambient temperature in a molar ratio of DFS to $Ca(OH)_2$ of from 1:3 to 1:4, an addition complex of the "sucrate" type is formed. A reducing agent, for example, sodium dithionite, is preferably also added to the suspension. After about 10 minutes, the solid phase is filtered and washed with water.

The serotonin present in the mother liquors is advantageously recovered. To this end, sulfuric acid is added until the solution has a pH of approximately 3, the calcium sulfate formed is eliminated, for example, by filtration, most of the water is eliminated, for example, by evaporation under reduced pressure, and, after the pH of the solution has been adjusted to approximately 10.8, the serotonin is extracted with an aliphatic alcohol containing from 4 to 8 carbon atoms or with a benzyl alcohol and then converted into the desired salt as described in the foregoing.

The insoluble complex $DFS.Ca(OH)_2$, constituting the solid phase mentioned above, is then suspended in water. The pH of the suspension is highly alkaline, i.e., from 12 to 13.

The calcium is precipitated in the form of a salt by treating the addition complex in aqueous suspension with a suitable acid. The choice of the acid is dictated by its ability to form, with the calcium, a salt which is insoluble in the aqueous media. The acid used may be an organic or mineral acid, for example, oxalic acid, citric acid, tartaric acid or phosphoric acid or, preferably, sulfuric acid, preferably concentrated. The insoluble calcium salts corresponding to the acids used, for example, $CaSO_4.2H_2O$ (gypsum) in the case of sulfuric acid, are precipitated.

Separation of the solid phase, for example, by filtration, leaves, for example, the oxalate, citrate, tartrate or even the hydrogenophosphate or, preferably, the neutral sulfate of DFS in solution.

In one preferred embodiment of the process according to the invention, in which the neutral sulfate of DFS is prepared in solution, a slight molar excess of creatinine and sulfuric acid are added to the solution as described above and the DFSCS is obtained by crystallization with alcohol.

After the solid phase has been dried and optionally recrystallized, for example, from a mixture of alcohol and water, the salt obtained contains approximately 90% of the theoretical quantity of DFS. Based on the serotonin used, the yield is of the order of 60%.

Calcium hydroxide is preferably added to the mother liquors, from which the alcohol has been eliminated by evaporation, the insoluble complex is separated, for example, by filtration, and recycled to the calcium hydroxide addition stage by incorporation in the following batch. Recycling of the $DFS.Ca(OH)_2$ complex enables the yield to be increased to approximately 70%. Washing of the complex and adding the washing waters to the mother liquors may also be performed.

By recovering the serotonin from the mother liquors after precipitation of the $DFS.Ca(OH)_2$ complex, the yield is increased to approximately 80%. By comparison, according to French Patent No. 2 317 937, the crude oxalate of DFS is obtained in amorphous form in a yield of approximately 25%.

The present invention also relates to a medicament containing DFSCS as active principle.

The medicament according to the invention is formulated according to the mode of administration.

If administered, for example in unit dosage form, by the oral or enteral route, the medicament may be formulated as a syrup, capsules, gelatin capsules, tablets or dragees.

For administration by the parenteral route, for example, the medicament may be formulated as a sterile and apyrogenic, physically and chemically stabilized solution or suspension.

For topical administration for example, the medicament may be formulated as a lotion, ointment, milk, cream or gel.

The concentration of the active principle may be form 10 to 50% by weight.

For example, a daily dose of from 400 to 450 mg taken in the form of gelatin capsules is suitable for the treatment of leprosy.

The invention is illustrated by the following Examples in which the percentages and parts are by weight, unless otherwise indicated.

EXAMPLE 1

2.36 g of serotonin hydrogenoacetate (10 mmoles), 3.6 g of anhydrous D-glucose (20 mmoles), 0.65 g of formic acid and 75 ml of anhydrous methanol are heated under nitrogen for 150 minutes to reflux temperature (60° C.). 50 ml of water are added and the methanol is eliminated by distillation in vacuo. The aqueous solution is decolored with 1.5 g of active carbon. After filtration, 0.9 g of creatinine (8 mmoles) and 2.8 g of 30% sulfuric acid are added to adjust the pH-value to 3, followed by concentration. 33 g of an orange-colored solution are thus obtained. After the gradual addition of 75 ml of 96% ethanol, a crystalline phase appears, being separated by filtration and then washed with 96% ethanol. After drying in vacuo at 40° C., 2.45 g of pale beige colored crystals are obtained. After recrystallization from water/ethanol, filtration and drying, white crystals corresponding to formula I above are collected in a yield of 2.12 g.

The structure was verified by proton and carbon NMR spectroscopy and by chemical analysis:

|  | Analysis (% by weight) | Theoretical (% by weight) |
|---|---|---|
| Total nitrogen | 12.12 | 11.97 |
| $H_2O$ (K. Fischer method) | 6.48 | 6.15 |
| Creatinine | 19.8 | 19.32 |
| $H_2SO_4$ (acidimetric method, METROHM ® titration curve) | 16.75 | 17.05 |

EXAMPLE 2

To 600 g of methanol are added 23.6 g of serotonin hydrogenoacetate (0.1 mole), 27.0 g of anhydrous D-glucose and 6.5 g of formic acid. This mixture is heated for 120 minutes in an inert atmosphere to reflux temperature. After this treatment, all the serotonin has reacted to form 25 g of DFS plus secondary products. 300 g of water are added to the reaction mixture after which the methanol is distilled in vacuo. 2.5 g of sodium dithionite and 30 g of calcium hydroxide (suspended in 50 g of water) are added to the acidic (pH 3.9) aqueous solution obtained. A solid phase appears. The mixture (pH 12.2) is stirred for 10 minutes and then filtered. The solid phase collected, which consists of the complex DFS.Ca(OH)$_2$ and an excess of Ca(OH)$_2$, is washed with water. The impurities and the salts are present in the filtrate.

The solid phase obtained as described above is suspended in 250 g of water. 95 g of 30% sulfuric acid are added, followed by stirring for 60 minutes. This treatment releases the DFS from its complex and precipitates the calcium in the form of gypsum (CaSO$_4$.2H$_2$O) which is separated by filtration. The filtrate (pH 6) containing the DFS in the form of its neutral sulfate is decolored while stirring with 5 g of active carbon. After filtration, 400 g of an orange-colored solution are obtained. 9.0 g of creatinine (0.08 mole) and 17 g of 30% sulfuric acid are then added to adjust the pH of this solution to 3. This solution of DFSCS is concentrated in vacuo to a weight of 170 g, after which 360 g of 96% ethanol are slowly added with stirring. A crystalline phase appears and, after stirring for 1 hour at ambient temperature, the crystals formed are filtered, washed with 150 g of 85% ethanol and then dried in vacuo at 40° C. 37.0 g of pale beige crystals are thus collected.

The mother liquor of crystallization is concentrated and the residual aqueous phase, which still contains 6.5 g of DFS, is treated in the same way as before. This requires 6 g of Ca(OH)$_2$ and then 17 g of 30% sulfuric acid. After concentration of the filtrate and addition of 2 g of creatinine, crystallization at pH 3 gives another 5.0 g of pale beige crystals.

The total obtained amounts to 42.0 g. This product has a DFS content of 52.5%. Recrystallization from water/ethanol gives 37.1 g of white crystals containing 55.4% of DFS and 20.8% of creatinine.

The yield of DFS is 20.5 g which corresponds to 60.6%, based on the serotonin used.

Analyses confirm the formula shown above.

EXAMPLE 3

The procedure is as in Example 2, except that the refluxing time is reduced to 40 minutes. At this stage of the reaction, only 80% of the serotonin used has reacted to form 27 g of DFS and impurities. Treatment with calcium hydroxide enables the DFS to be separated from the unreacted serotonin, the serotonin remaining soluble in the filtrate and being capable of being extracted.

To this end, the filtrate is concentrated in vacuo to a volume of 150 ml and then acidified to pH 3 with 30% sulfuric acid. The calcium sulfate formed (CaSO$_4$.2H$_2$O) is separated by filtration. The pH of the filtrate, in which the serotonin is present, is adjusted to 10.8 (isoelectric point of serotonin) by the addition of sodium hydroxide, after which the serotonin is extracted with 3×100 ml of isobutanol. After elimination of the aqueous phase, the 3 isobutanol extracts are combined, neutralized to pH 6 with acetic acid and then concentrated in vacuo. 4.0 g of serotonin hydrogenoacetate are thus collected, corresponding to 16.6% of the serotonin used.

After the various treatments described in Example 2, the solid phase (the DFS.Ca(OH)$_2$ complex) gives 45 g of white crystals containing 52% of DFS. The yield of DFS amounts of 69%. By recycling the serotonin, the yield is increased to 81%.

We claim:

1. A process for preparing a double sulfate salt of 1-desoxy-(5-hydroxytryptamino)-D-fructose and 1- methylhydantoin-2-imide comprising adding 1-methyl-hydantoin-2-imide to an aqueous solution of 1-desoxy-(5-hydroxytryptamino)-D-fructose and sulfuric acid having a pH of approximately 3 for forming a reaction medium including the double sulfate salt and then separating the double sulfate salt from mother liquor of the reaction medium.

2. A process as claimed in claim 1 further comprising concentrating the reaction medium and then adding a water-miscible solvent, in which the double sulfate salt is insoluble, to the concentrated reaction medium for crystallizing the double sulfate salt from the mother liquid and then separating the crystallized double sulfate salt from the mother liquor.

3. A process as claimed in claim 2 wherein the water-miscible solvent is selected from the group consisting of acetone and $C_1$ through $C_4$ alcohols.

4. A process as claimed in claim 2 wherein the water-miscible solvent is ethanol.

5. A process as claimed in claim 1 further comprising after separating the double sulfate salt from the mother liquor of the reaction medium, adding calcium hydroxide to the mother liquor for obtaining an insoluble complex, separating the complex from mother liquor of the complex and then preparing 1-desoxy-(5-hydroxytryptamino)-D-fructose and the aqueous solution from the complex.

6. A process as claimed in claim 5 further comprising adding an acid to the complex for precipitating a calcium salt, separating the precipitated salt from mother liquor of the salt and then preparing the aqueous solution with the mother liquor of the salt.

7. A process as claimed in claim 5 further comprising after separating the complex from its mother liquor, treating the motor liquor of the complex with sulfuric acid for precipitating calcium sulfate, eliminating the calcium sulfate from the mother liquor of the complex and adjusting the pH of the mother liquor of the complex to the isoelectric point of 5-hydroxytryptamine, extracting 5-hydroxytryptamine from the pH adjusted mother liquor with an alcohol selected from the group consisting of a benzyl alcohol and an aliphatic alcohol containing from 4 to 8 carbon atoms, eliminating the alcohol from the extracted 5-hydroxytryptamine and then preparing 1-desoxy-(5-hydroxytryptamino)-D-fructose and the aqueous solution from the extracted 5-hydroxytryptamine.

8. A process as claimed in claim 1 further comprising after separating the double sulfate salt from the mother liquor, extracting 5-hydroxytryptamine from the mother liquor by a process selected from the group consisting of ion exchange and solvent extraction and then preparing 1-desoxy-(5-hydroxytryptamino)-D-fructose and the aqueous solution from the 5-hydroxytryptamine.

9. A process as claimed in claim 1 further comprising after separating the double sulfate salt from the mother liquor, adjusting the pH of the mother liquor to the isoelectric point of 5-hydroxytryptamine, extracting 5-hydroxytryptamine from the pH adjusted mother liquor with an alcohol selected from the group consisting of a benzyl alcohol and an aliphatic alcohol containing from 4 to 8 carbon atoms, eliminating the alcohol from the 5-hydroxytryptamine and then preparing 1-desoxy-(5-hydroxytryptamino)-D-fructose and the aqueous solution from the 5-hydroxytryptamine.

10. A process as claimed in claim 9 further comprising after eliminating the alcohol from the 5-hydroxytryptamine, adding an excess of calcium hydroxide to the 5-hydroxytryptamine in the presence of water for obtaining an insoluble complex, separating the complex from its mother liquor, adding an acid to the complex for precipitating a calcium salt, separating the precipitated calcium salt from mother liquor of the salt and then preparing the aqueous solution with the mother liquor of the salt.

11. A process as claimed in claim 10 wherein the calcium-precipitating acid is selected from the group consisting of oxalic acid, citric acid, tartaric acid, phosphoric acid and sulfuric acid.

12. A process as claimed in claim 10 further comprising separating the complex from its mother liquor, treating the mother liquor of the complex with sulfuric acid for precipitating calcium sulfate, eliminating the calcium sulfate from the mother liquor of the complex and adjusting the pH of the mother liquor of the complex to the isoelectric point of 5-hydroxytryptamine, extracting 5-hydroxytryptamine from the pH adjusted mother liquor with an alcohol selected from the group consisting of a benzyl alcohol and an aliphatic alcohol containing from 4 to 8 carbon atoms, eliminating the alcohol from the extracted 5-hydroxytryptamine and then preparing 1-desoxy-(5-hydroxytryptamino)-D-fructose and the aqueous solution from the extracted 5-hydroxytryptamine.

13. A process as claimed in claim 12 further comprising washing the separated insoluble complex with water and adding the washing water to the mother liquor of the complex.

14. A process as claimed in claim 1 further comprising condensing D-glucose with 5-hydroxytryptamine in a reaction mixture of an anhydrous solvent in the presence of a catalyst selected from the group consisting of acids and bases in an inert atmosphere and then eliminating the solvent from the reaction mixture and then preparing 1-desoxy-(5-hydroxytryptamino)-D-fructose and the aqueous solution.

15. A process as claimed in claim 14 further comprising adding water to the anhydrous solvent reaction medium prior to eliminating the solvent.

16. A process as claimed in claim 14 wherein the catalyst is an acid selected from mono- and poly-carboxylic acids which are present in a quantity sufficient for enabling a pH of from 3 to 5 for the anhydrous solvent reaction medium.

17. A process as claimed in claim 16 wherein the catalyst is selected from the group of acids consisting of formic acid, oxalic acid and acetic acid.

18. A process for preparing an aqueous solution of 1-desoxy-(5-hydroxytryptamino)-D-fructose and sulfuric acid comprising reacting a mixture of an excess of calcium hydroxide with 1-desoxy-(5-hydroxytryptamino)-D-fructose in the presence of water for forming an insoluble addition complex in the reaction mixture and then adding an acid to the reaction mixture for precipitating a calcium salt from mother liquor of the reaction mixture, separating the precipitated calcium salt from the mother liquor and then adding sulfuric acid to the mother liquor.

19. A process for preparing 5-hydroxytryptamine comprising reacting a mixture of an excess of calcium hydroxide with 1-desoxy-(5-hydroxytryptamino)-D-fructose in the presence of water for obtaining an insoluble complex in the reaction mixture, separating the complex from mother liquor of the reaction mixture and adding sulfuric acid to the mother liquor for forming a calcium salt, separating the calcium salt from the mother liquor, adjusting the pH of the mother liquor to the isoelectric point of 5-hydroxytryptamine, extracting 5-hydroxytryptamine with an alcohol selected from the group consisting of a benzyl alcohol and an aliphatic alcohol containing from 4 to 8 carbon atoms eliminating the alcohol from the 5-hydroxytryptamine.

20. A process as claimed in claim 19 further comprising washing the separated insoluble complex with water and adding the washing water to the mother liquor.

21. A process as claimed in claim 18 wherein the sulfuric acid is added to the mother liquor in an amount sufficient for enabling a pH of about 3.

* * * * *

UNITED STATES PATENT AND TRADEMARK OFFICE
CERTIFICATE OF CORRECTION

PATENT NO. : 4,925,932
DATED : May 15, 1990
INVENTOR(S) : Raymond BERTHOLET, et al.

It is certified that error appears in the above-identified patent and that said Letters Patent is hereby corrected as shown below:

Column 1, line 42, after "1-desoxy-" and before "5", insert a parenthesis. Thus, Column 1, line 42, should read "1-desoxy-(5-hydroxytryptamino)".

Column 5, line 5, insert a coma after "example", and delete the coma after "form".

Column 7, line 13 (line 6 of claim 2), liquid" should be --liquor--.

Column 7, line 35 (line 3 of claim 7), "motor" should be --mother--.

Signed and Sealed this

Thirteenth Day of August, 1991

Attest:

HARRY F. MANBECK, JR.

*Attesting Officer*    *Commissioner of Patents and Trademarks*